United States Patent
Xu et al.

(10) Patent No.: US 11,834,420 B2
(45) Date of Patent: Dec. 5, 2023

(54) PREPARATION METHOD OF PYRIMIDINYLTHIO-BENZOATE OXIME ESTER COMPOUND AND APPLICATION THEREOF AS HERBICIDE

(71) Applicant: CHANGZHOU UNIVERSITY, Changzhou (CN)

(72) Inventors: Defeng Xu, Changzhou (CN); Xiangjian Xu, Changzhou (CN); Hang Hu, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 401 days.

(21) Appl. No.: 17/258,752

(22) PCT Filed: May 26, 2020

(86) PCT No.: PCT/CN2020/092353
§ 371 (c)(1),
(2) Date: Jan. 8, 2021

(87) PCT Pub. No.: WO2021/017597
PCT Pub. Date: Feb. 4, 2021

(65) Prior Publication Data
US 2021/0221773 A1 Jul. 22, 2021

(30) Foreign Application Priority Data
Jul. 30, 2019 (CN) .......................... 201910692337.6

(51) Int. Cl.
*C07D 239/60* (2006.01)
*A01N 43/54* (2006.01)

(52) U.S. Cl.
CPC ........... *C07D 239/60* (2013.01); *A01N 43/54* (2013.01)

(58) Field of Classification Search
None
See application file for complete search history.

(56) References Cited

U.S. PATENT DOCUMENTS 5,494,888 A * 2/1996 Hur ...................... C07D 405/12
504/225

FOREIGN PATENT DOCUMENTS

| CN | 1931846 A | 3/2007 | |
|---|---|---|---|
| CN | 103333121 A | 10/2013 | |
| CN | 104302629 A | 1/2015 | |
| CN | 110317177 A | 10/2019 | |
| WO | WO-2015081493 A1 * | 6/2015 | ............. A01N 43/54 |

OTHER PUBLICATIONS

Engineeringtoolbox (https://web.archive.org/web/20171216034527/https://www.engineeringtoolbox.com/stp-standard-ntp-normal-air-d_772.html, no pagination) (Year: 2017).*
Harper college (https://web.archive.org/web/20180301184046/http://dept.harpercollege.edu/chemistry/chm/100/dgodambe/thedisk/labtech/filter.htm), 1 pg. (Year: 2017).*
Patani et al. (Chem. Rev., 1996, 96, 3147-3176) (Year: 1996).*
Alan Wood Pyrithiobac entry (https://web.archive.org/web/20080729201504/http://www.alanwood.net/pesticides/index_cn_frame.html), 1 pg. (Year: 2008).*
Xiangjian Xu, et al., Synthesis and Herbicidal Activities of Novel Substituted Acetophenone Oxime Esters of Pyrithiobac, Chemistry Select, 2020, pp. 69-74, 5.
Zhang Te, et al., Advances in pyrimidinyl(oxy)thiobenzoic acid herbicides, Plant Protection, 2018, pp. 22-28, 44(2).

* cited by examiner

*Primary Examiner* — Erin E Hirt
(74) *Attorney, Agent, or Firm* — Bayramoglu Law Offices LLC

(57) ABSTRACT

A preparation method of a pyrimidinylthio-benzoate oxime ester compound and an application thereof are provided. The chemical structural formula of the pyrimidinylthio-benzoate compound is shown in the following formula (1). The preparation method includes step A: preparation of a substituted acetophenone oxime: taking hydroxylamine hydrochloride and a substituted acetophenone as a raw material, adding an alcohol as a solvent, and performing a reaction at 0° C.-80° C. for 1-5 hours under an alkaline condition to obtain the substituted acetophenone oxime; and step B: preparation of the compound: using 2-chloro-6-((4,6-dimethoxypyrimidin-2-yl)thio)benzoic acid and the substituted acetophenone oxime as a raw material, and performing a reaction under an action of an organic solvent, a dehydrating agent and a catalyst at 25° C. for 6-24 hours; after the reaction is completed, performing a suction filtration, and subjecting the filtrate to a decompression distillation and a recrystallization to obtain the compound.

formula (I)

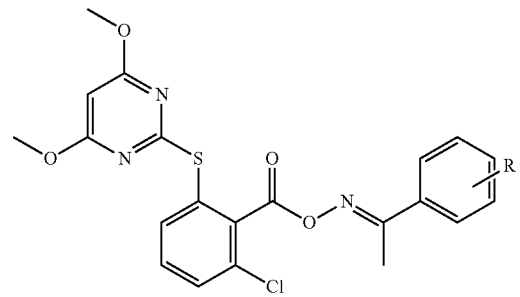

5 Claims, No Drawings

PREPARATION METHOD OF PYRIMIDINYLTHIO-BENZOATE OXIME ESTER COMPOUND AND APPLICATION THEREOF AS HERBICIDE

CROSS REFERENCE TO THE RELATED APPLICATIONS

This application is the national phase entry of International Application No. PCT/CN2020/092353, filed on May 26, 2020, which is based upon and claims priority to Chinese Patent Application No. 201910692337.6, filed on Jul. 30, 2019, the entire contents of which are incorporated herein by reference.

TECHNICAL FIELD

The present invention belongs to the technical field of herbicides, and relates to an application of herbicides in selective control of gramineous weeds and broadleaf weeds in crops. The present invention particularly relates to a preparation method of a pyrimidinylthio-benzoate oxime ester compound and an application thereof as a herbicide.

BACKGROUND

Acetolactate synthase (ALS) inhibitor is a herbicide type developed in the 1980s, which controls weeds by inhibiting the biosynthesis of amino acids. The ALS inhibitor has the characteristics of broad spectrum activity, high efficiency, low toxicity, and others, and has been widely used for weed. In recent years, a large number of inhibitors targeting ALS have been developed. In terms of chemical structure, such herbicides mainly include sulfonylureas (SU), imidazolinones (IMI), triazolopyrimidines (TP), pyrimidinylthio-benzoates (PTB), and other compounds. Compared with other ALS inhibitors, the structural changes of pyrimidinylthio-benzoates are more flexible.

Pyrimidinylthio-benzoate herbicides are the new herbicides first developed by Kumiai Chemical Industry Co., Ltd., Japan. These herbicides have a significant effect on a wide range of gramineous weeds and broadleaf weeds in rice fields. The greatest commercial potential of pyrimidinylthio-benzoate herbicides is that they can selectively control barnyard grass (*Echinochloa crusgalli*) with extremely low dosage and wide application range, thus attracting more and more attention. The commercial varieties of pyrimidinylthio-benzoate herbicides mainly include bispyribac-sodium, pyriminobac-methyl, pyribenzoxim, pyrithiobac-sodium and pyriftalid. Among them, pyrithiobac-sodium is the first commercialized variety, and it is also a special herbicide for cotton fields, which is highly safe for cotton. Pyrithiobac-sodium can control annual and perennial gramineous weeds and most broadleaf weeds. It has a good control effect on refractory weeds, such as morning glory (*Pharbitis nil* (Linn.) Choisy), Siberian cocklebur (*Xanthium sibiricum* Patrin ex Widder), Velvetleaf (*Abutilon theophrasti* Medicus), prickly fanpetals (*Sida spinosa* L.), Aleppo grass (*Sorghum halepense*), and more.

Due to the single target of ALS inhibitors, continuous use can easily induce weeds to develop resistance. With the widespread use of the pyrithiobac-sodium herbicide, the problem of weed resistance has become more and more prominent. In response to this problem, the discovery and development of new pyrimidinylthio-benzoate derivatives with low dosage and high activity is of great significance and can provide more choices for herbicides.

SUMMARY

The first objective of the present invention is to provide a novel pyrimidinylthio-benzoate compound with high herbicidal activity aiming at the problem of weed resistance induced by the pyrithiobac-sodium herbicide in cotton fields.

The second objective of the present invention is to provide a preparation method of the novel pyrimidinylthio-benzoate compound with high herbicidal activity.

The third objective of the present invention is to provide an application of the pyrimidinylthio-benzoate compound in preparing a herbicide.

In order to achieve the first objective, the technical solution adopted by the present invention is as follows: a novel pyrimidinylthio-benzoate compound with high herbicidal activity, a chemical structural formula of the compound is shown in the following general formula (I):

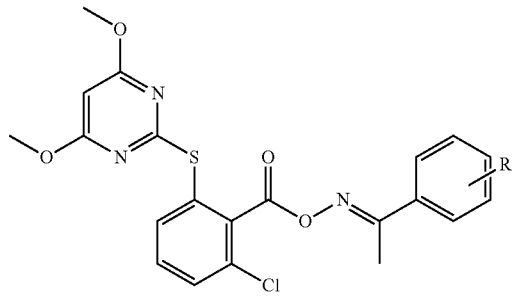

R is o, m, p-CH$_3$, CF$_3$, NO$_2$, F or 2,4-2OCH$_3$     (I)

wherein R is an ortho-, meta-, and para-methyl group, a trifluoromethyl group, a nitro group, fluorine or a 2,4-dimethoxy group.

The novel pyrimidinylthio-benzoate compound with high herbicidal activity, preferably chemical names and chemical structural formulas thereof are as follows:

A: (E)-1-(o-tolyl)ethan-1-one O-(2-chloro-6-((4,6-dimethoxypyrimidin-2-yl)thio)benzoyl) oxime

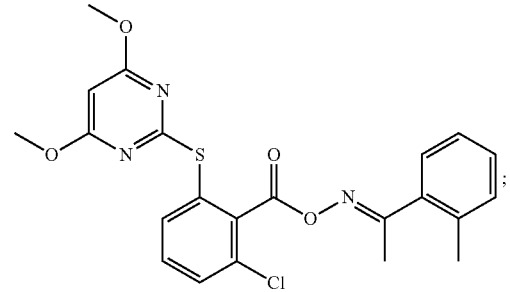

B: (E)-1-(o-tolyl)ethan-1-one O-(2-chloro-6-((4,6-dimethoxypyrimidin-2-yl)thio)benzoyl) oxime

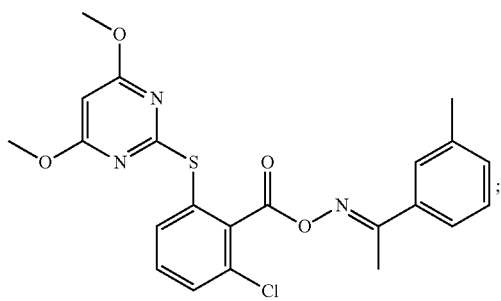 [SMILES: COc1cc(OC)nc(Sc2cccc(Cl)c2C(=O)O/N=C(\C)c2cccc(C)c2)n1]

C: (E)-1-(p-tolyl)ethan-1-one O-(2-chloro-6-((4,6-dimethoxypyrimidin-2-thio)benzoyl) oxime

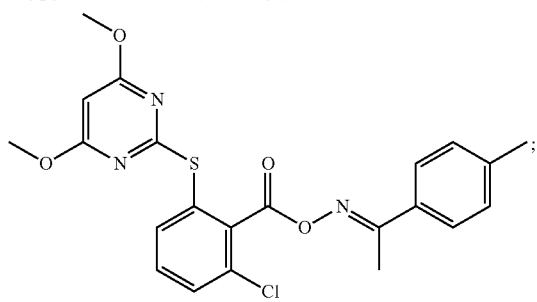

D: (E)-1-(2-(trifluoromethyl)phenyl)ethan-1-one O-(2-chloro-6-((4,6-dimethoxypyrimidin-2-yl)thio)benzoyl)oxime

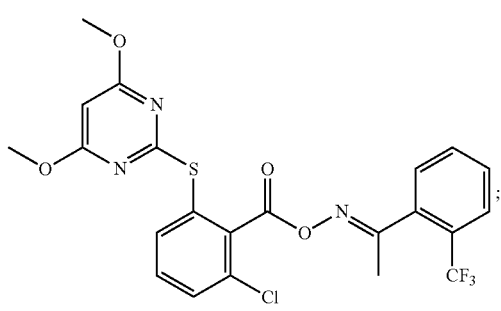 [SMILES: COc1cc(OC)nc(Sc2cccc(Cl)c2C(=O)O/N=C(\C)c2ccccc2C(F)(F)F)n1]

E: (E)-1-(3-(trifluoromethyl)phenyl)ethan-1-one O-(2-chloro-6-((4,6-dimethoxypyrimidin-2-yl)thio)benzoyl)oxime

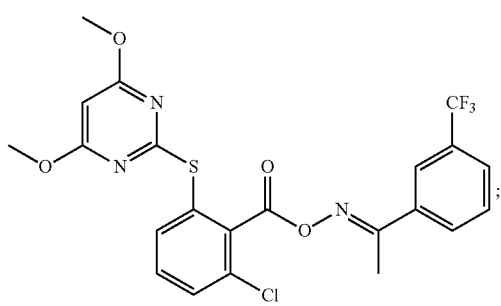 [SMILES: COc1cc(OC)nc(Sc2cccc(Cl)c2C(=O)O/N=C(\C)c2cccc(C(F)(F)F)c2)n1]

F: (E)-1-(4-(trifluoromethyl)phenyl)ethan-1-one O-(2-chloro-6-4,6-dimethoxypyrimidin-2-yl)thio)benzoyl)oxime

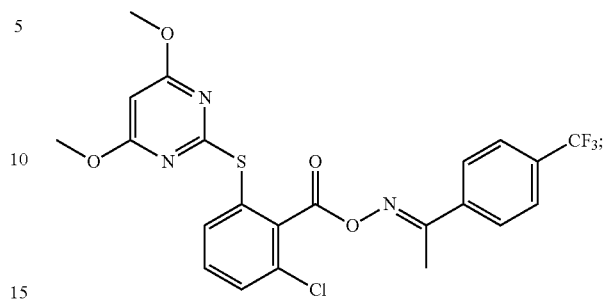

G: (E)-1-(2-nitrophenyl)ethan-1-one O-(2-chloro-6-4,6-dimethoxypyrimidin-2-thio)benzoyl)oxime

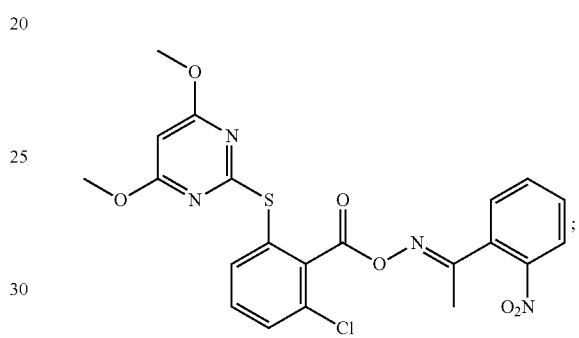

H: (E)-1-(3-nitrophenyl)ethan-1-one O-(2-chloro-6-(4,6-dimethoxypyrimidin-2-yl)thio)benzoyl)oxime

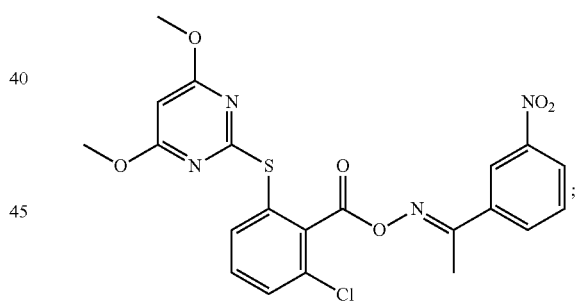

I: (E)-1-(4-nitrophenyl)ethan-1-one O-(2-chloro-6((4,6-dimethoxypyrimidin-2-yl)thio)benzoyl)oxime

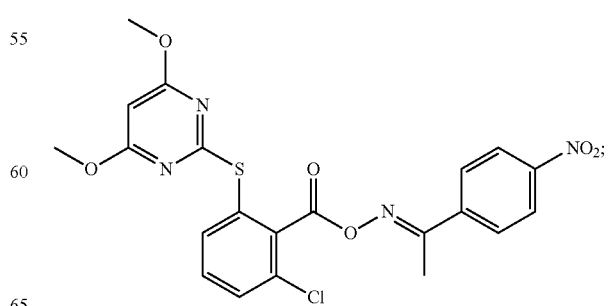

J: (E)-1-(2-fluorophenyl)ethan-1-one O-(2-chloro-6-4,6-dimethoxypyrimidin-2-yl)thio)benzoyl) oxime

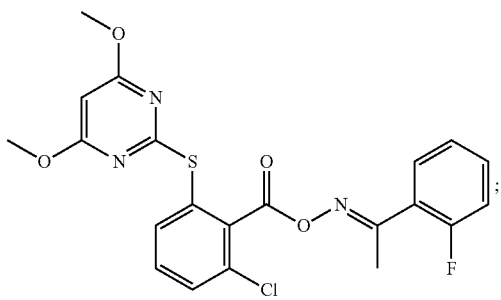

K: (E)-1-(3-fluorophenyl)ethan-1-one O-(2-chloro-6-((4,6-dimethoxypyrimidin-2-yl)thio)benzoyl) oxime

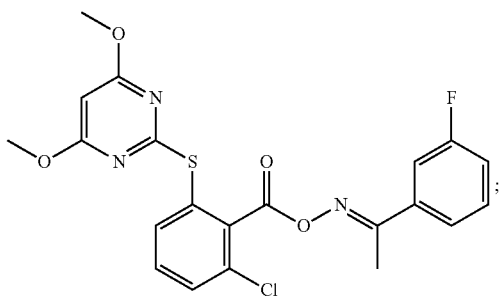

L: (E)-1-(4-fluorophenyl)ethan-1-one O-(2-chloro-6-(4,6-dimethoxypyrimidin-2-yl)thio)benzoyl) oxime

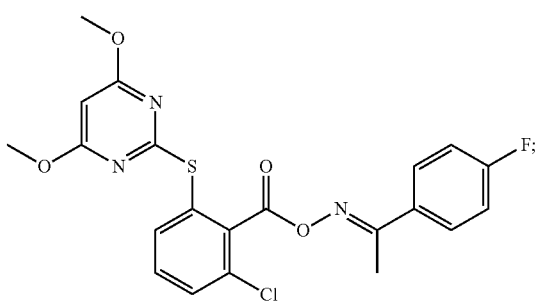 [SMILES: COc1cc(OC)nc(Sc2cccc(Cl)c2C(=O)O/N=C(\C)c2ccc(F)cc2)n1]

and

M: (E)-1-(2,4-dimethoxyphenyl)ethan-1-one O-(2-chloro-6-((4,6-dimethoxypyrimidin-2-yl)thio)benzoyl)oxime

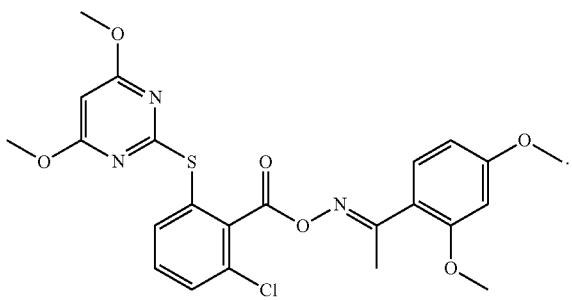

In order to achieve the second objective, the technical solution adopted by the present invention is as follows: a preparation method of the pyrimidinylthio-benzoate compound includes the following steps:

step A: preparation of a substituted acetophenone oxime: taking hydroxylamine hydrochloride and a substituted acetophenone as a raw material, adding an alcohol as an alcohol solvent, and reacting at 0° C.-80° C. for 1-5 hours under an alkaline condition to obtain the substituted acetophenone oxime; and step B: preparation of the compound of formula (I): using 2-chloro-6-4,6-dimethoxypyrimidin-2-yl)thio)benzoic acid and the substituted acetophenone oxime as a raw material, and reacting under the action of an organic solvent, a dehydrating agent and a catalyst at 25° C. for 6-24 hours; after the reaction is completed, performing a suction filtration to obtain a filtrate, and subjecting the filtrate to a decompression distillation and a recrystallization to obtain the compound of formula (I).

The alcohol solvent in step A is one selected from the group consisting of methanol, ethanol and isopropanol.

An alkali for the alkaline condition in step A is one selected from the group consisting of sodium hydroxide, sodium carbonate, sodium acetate, triethylamine and pyridine.

A molar ratio of the substituted acetophenone, the hydroxylamine hydrochloride, the alkali, and the alcohol in step A is 1:1.5:1.5:8.

The organic solvent in step B is dichloromethane.

The dehydrating agent in step B is one selected from the group consisting of N,N'-dicyclohexylcarbodiimide (DCC), 1-(3-dimethylaminopropyl)-3-ethylcarbodiimide hydrochloride (EDCI) and N,N'-diisoproplylcarbodiimide (DIC).

The catalyst in step B is one selected from the group consisting of 4-dimethylaminopyridine (DMAP), 4-(1'-tetrahydro pyrrole)pyridine (4-PPY) and 1-hydroxybenzotriazole (HOBt).

A molar ratio of the 2-chloro-6((4,6-dimethoxypyrimidin-2-yl)thio)benzoic acid, the substituted acetophenone oxime, the dehydrating agent, the catalyst, and the organic solvent in step B is 1:1:1.2:0.06:9.

The reaction formula of the preparation method is as follows:

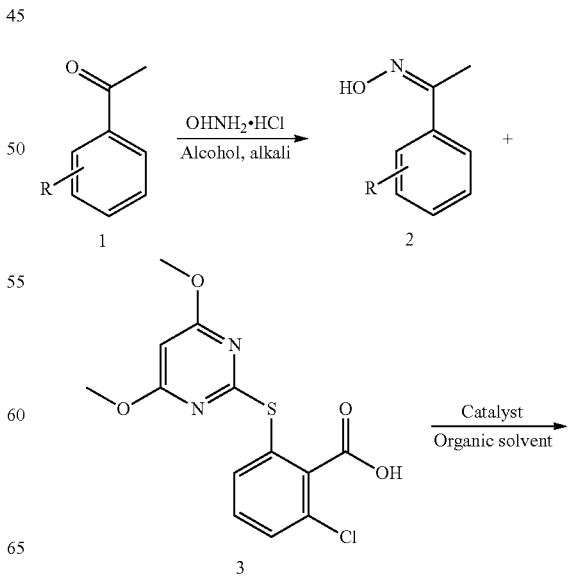

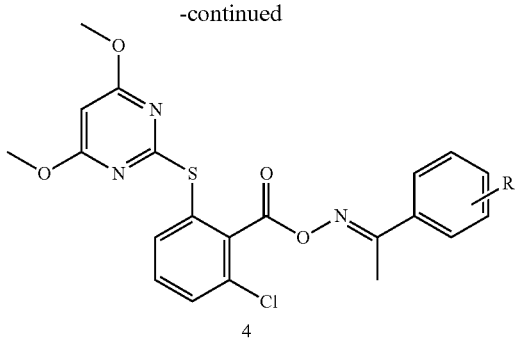

4

In order to achieve the third objective, the technical solution adopted by the present invention is as follows: an application of the novel pyrimidinylthio-benzoate compound in weed control.

The herbicide is used to control barnyard grass (*Echinochloa crusgalli*), goose grass (*Eleusine indica*), green bristlegrass (*Setaria viridis*), redroot amaranth (*Amaranthus retroflexus*), purslane (*Portulaca oleracea*), and lambsquarters (*Chenopodium album*).

The advantages of the present invention are as follows.
1. The present invention provides a series of novel pyrimidinylthio-benzoate oxime ester compounds with high efficiency, safety and herbicidal activity, which are very effective in controlling weeds such as barnyard grass (*Echinochloa crusgalli*), goose grass (*Eleusine indica*), green bristlegrass (*Setaria viridis*), redroot amaranth (*Amaranthus retroflexus*), purslane (*Portulaca oleracea*) and lambsquarters (*Chenopodium album*), and others, have low dosage and broad-spectrum effect, and are environment-friendly, low-toxic, and especially safe for crop cotton.
2. The present invention provides a preparation method of the novel pyrimidinylthio-benzoate compounds with high efficiency, safety and herbicidal activity, which can prepare a large amount of the pyrimidinylthio-benzoate compounds with high yield and good purity.

DETAILED DESCRIPTION OF THE EMBODIMENTS

The specific embodiments provided by the present invention are described in detail below.

Embodiment 1: Preparation of 2-methylacetophenone oxime 2-methyl acetophenone (10.0 g, 74.5 mmol), hydroxylamine hydrochloride (7.8 g, 112 mmol) and 80 mL of methanol are added to a 250 mL reaction flask, and then a 20% sodium hydroxide aqueous solution (22.4 g, 112 mmol) is added dropwise, and a reflux reaction is performed at 65° C. for 2 hours. After the reaction, the solvent is evaporated under decompression, washed with water, filtered with suction, and dried to obtain 10.2 g of white solid 2-methylacetophenone oxime, with a yield of 91.8%.

Embodiment 2: Preparation of (E)-1-(o-tolyl)ethan-1-one O-(2-chloro-6-4,6-dimethoxypyrimidin-2-yl)thio)benzoyl) oxime (A)

2-chloro-6-((4,6-dimethoxypyrimidin-2-yl)thio)benzoic acid (10.0 g, 30.6 mmol), EDCI (7.0 g, 36.7 mmol), HOBt (0.21 g, 1.5 mmol), and 90 mL of dichloromethane are added in a 250 mL reaction flask, then 2-methylacetophenone oxime (4.6 g, 30.6 mmol) in dichloromethane is added dropwise, and then reacted at 25° C. for 6 hours. After the reaction is completed, a suction filtration is performed first, and the filtrate is subjected to decompression distillation and recrystallization to obtain 10.5 g of white solid (E)-1-(o-tolyl)ethan-1-one O-(2-chloro-6-((4,6-dimethoxypyrimidin-2-yl)thio)benzoyl) oxime, with a yield of 77.26%, and a melting point of 108° C.-111° C.

$^1$H NMR (400 MHz, CDCl$_3$): δ 7.64 (d, J=7.7 Hz, 1H), 7.50 (d, J=8.0 Hz, 1H), 7.41 (t, J=7.9 Hz, 1H), 7.27 (d, J=7.2 Hz, 1H), 7.23 (d, 1H), 7.21-7.15 (m, 2H), 5.68 (s, 1H), 3.68 (s, 6H), 2.31 (s, 3H), 2.18 (s, 3H).
$^{13}$C NMR (75 MHz, CDCl$_3$): δ 180.88, 169.18, 166.61, 163.65, 138.34, 136.16, 135.90, 135.23, 131.44, 130.80, 130.39, 130.37, 129.45, 129.34, 128.23, 125.84, 86.56, 54.07, 20.10, 17.99.

Embodiment 3: Preparation of 3-methylacetophenone oxime 3-methylacetophenone (10.0 g, 74.5 mmol), hydroxylamine hydrochloride (7.8 g, 112 mmol) and 80 mL of ethanol are added to a 250 mL reaction flask, and then a 20% sodium carbonate aqueous solution (59.0 g, 112 mmol) is added dropwise, and then reacted at 25° C. for 4 hours. After the reaction, the solvent is evaporated under decompression, washed with water, filtered with suction, and dried to obtain 10.4 g of white solid 3-methylacetophenone oxime, with a yield of 93.6%.

Embodiment 4: Preparation of (E)-1-(m-tolyl)ethan-1-one O-(2-chloro-6((4.6-dimethoxypyrimidin-2-yl)thio)benzoyl) oxime (B)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 3-methylacetophenone oxime (4.6 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 10.8 g of white solid (E)-1-(m-tolyl)ethan-1-one O-(2-chloro-6-((4,6-dimethoxypyrimidin-2-yl)thio)benzoyl) oxime, with a yield of 79.5%, and a melting point of 84° C.-88° C.

$^1$NMR (400 MHz, CDCl$_3$): δ 7.65 (d, J=7.3 Hz, 1H), 7.57 (s, 1H), 7.51 (d, J=7.6 Hz, 1H), 7.49-7.39 (m, 2H), 7.29-7.22 (m, 2H), 5.68 (s, 1H), 3.69 (s, 6H), 2.35 (s, 3H), 2.23 (s, 3H).
$^{13}$C NMR (75 MHz, CDCl$_3$): δ 180.87, 169.15, 164.41, 163.34, 138.32, 138.21, 136.15, 13436, 131.60, 131.58, 130.42, 130.40, 129.47, 128.43, 127.72, 124.36, 86.59, 54.10, 21.38, 14.58.

Embodiment 5: Preparation of 4-methylacetophenone oxime 4-methylacetophenone (10.0 g, 74.5 mmol), hydroxylamine hydrochloride (7.8 g, 112 mmol) and 80 mL of ethanol are added to a 250 mL reaction flask, and then a 20% sodium acetate aqueous solution (59 g, 112 mmol) is added dropwise, and then reacted at 25° C. for 3 hours. After the reaction, the solvent is evaporated under decompression, washed with water, filtered with suction, and dried to obtain 10.3 g of white solid 4-methylacetophenone oxime, with a yield of 92.7%.

Embodiment 6: Preparation of (E)-1-(p-tolyl)ethan-1-one O-(2-chloro-6-((4,6-dimethoxypyrimidin-2-yl)thio)benzoyl) oxime (C)

2-chloro-6-((4,6-dimethoxypyrimidin-2-yl)thio)benzoic acid (10.0 g, 30.6 mmol), DIC (4.6 g, 36.7 mmol), 4-PPY (0.22 g, 1.5 mmol), and 90 mL of dichloromethane are added in a 250 mL reaction flask, then 4-methylacetophenone oxime (4.6 g, 30.6 mmol) in dichloromethane is added dropwise, and then reacted at 25° C. for 20 hours. After the reaction is completed, a suction filtration is performed first, and the filtrate is subjected to decompression distillation and recrystallization to obtain 10.6 g of white solid (E)-1-(p-tolyl)ethan-1-one O-(2-chloro-6-((4,6-dimethoxypyrimidin-2-yl)thio)benzoyl) oxime, with a yield of 78.0%, and a melting point of 115° C.-119° C.

$^1$H NMR (400 MHz, CDCl$_3$): δ 7.66 (dd, J=7.7, 1.0 1Hz, 1H), 7.62 (d, J=8.2 Hz, 2H), 7.52 (dd, J=8.1, 1.1 Hz, 1H), 7.43 (t, J=7,9 Hz, 1H), 7.19 (d, J=8.1 Hz, 2H), 5.69 (s, 1H) 3.80 (s, 6H), 2.37 (s, 3H), 2.24 (s, 3H).

$^{13}$C NMR (75 MHz, CDCl$_3$): δ 180.87, 169.14, 164.01, 163,48, 141.13, 138.26, 136.1, 131.53, 131.51, 130.41, 130.38, 129.40, 129.25, 127.09, 86.59, 54.09, 21.42, 14.35.

Embodiment 7: Preparation of 2-trifluoromethlyl acetophenone oxime 2-trifluoromethyl acetophenone (10.0 g, 53.1 mmol), hydroxylamine hydrochloride (5.5 g, 79.7 mmol) and 80 mL of methanol are added to a 250 mL reaction flask, and then a 20% sodium hydroxide aqueous solution (15.9 g, 79.7 mmol) is added dropwise, and a reflux reaction is performed at 65° C. for 2 hours. After the reaction, the solvent is evaporated under decompression, washed with water, filtered with suction, and dried to obtain 10.2 g of white solid 2-trifluoromethyl acetophenone oxime, with a yield of 94.4%.

Embodiment 8: Preparation of (E)-1-(2-(trifluoromethyl)phenyl)ethan-1-one O-(2-chloro-6-((4,6-dimethoxypyrimidin-2-yl)thio)benzoyl)oxime (D)

2-chloro-6-((4,6-dimethoxypyrimidin-2-yl)thio)benzoic acid (10.0 g, 30.6 mmol), EDCI (7.0 g, 36.7 mmol), HOBt (0.21 g, 1.5 mmol), and 90 mL of dichloromethane are added in a 250 mL reaction flask, then 2-trifluoromethyl acetophenone oxime (6,2 g, 30.6 mmol) in dichloromethane is added dropwise in ice bath, and then reacted at 25° C. for 6 hours. After the reaction is completed, a suction filtration is performed first, and the filtrate is subjected to decompression distillation and recrystallization to obtain 12.0 g of white solid (E)-1-(2-(trifluoromethyl)phenyl)ethan-1-one O-(2-chloro-6-((4,6-dimethoxypyrimidin-2-yl)thio)benzoyl)oxime, with a yield of 76.9%, and a melting point of 82° C.-85° C.

$^1$H NMR (400 MHz, CDCl$_3$): δ 7.84 (d, J=7.7 Hz, 1H), 7.76-7.69 (m, 2H), 7.62-7.54 (m, 2H), 7.36 (t, J=8.3 Hz, 1H), 7.21 (d, J=7.9 Hz, 1H), 5.80 (s, 1H), 3.80 (s, 6H), 2.29 (s, 3H).

$^{13}$C NMR (75 MHz, CDCl$_3$): δ 180.90, 169.02, 163.14, 162.86, 137.90, 137.68, 136.20, 132.73, 131.82, 131.02 (q, J=3.8 Hz), 130.18, 129.60, 128.64 (d, J=2.4 Hz), 127.46 (d, J=2.8 Hz), 126.24 (q, J=27.1 Hz), 124.10 (q, J=4.0 Hz), 123.43 (q, J=14.6 HZ), 86.62, 54.12, 13.46.

Embodiment 9: Preparation of 3-trifluoromethyl acetophenone oxime 3-trifluoromethyl acetophenone (10.0 g, 53.1 mmol), hydroxylamine hydrochloride (5.5 g, 79.7 mmol) and 80 mL of methanol are added to a 250 mL reaction flask, and then a 20% sodium hydroxide aqueous solution (15.9 g, 79.7 mmol) is added dropwise, and reacted at 25° C. for 4 hours. After the reaction, the solvent is evaporated under decompression, washed with water, filtered with suction, and dried to obtain 10.1 g of white solid 3-trifluoromethyl acetophenone oxime, with a yield of 93.5%.

Embodiment 10: Preparation of (E)-1-(3-(trifluoromethyl)phenyl)ethan-1-one O-(2-chloro-6-((4,6-dimethoxypyrimidin-2-yl)thio)benzoyl)oxime (E)

2-chloro-6-((4,6-dimethoxypyrimidin-2-yl)thio)benzoic acid (10.0 g, 30.6 mmol), EDCI (7.0 g, 36.7 mmol), HOBt (0.21 g, 1.5 mmol), and 90 mL of dichloromethane are added in a 250 mL reaction flask, then 3-trifluoromethyl acetophenone oxime (6.2 g, 30.6 mmol) in dichloromethane is added dropwise in an ice bath, and then reacted at 25° C. for 6 hours. After the reaction is completed, a suction filtration is performed first, and the filtrate is subjected to decompression distillation and recrystallization to obtain 11.6 g of white solid (E)-1-(3trifluoromethyl)phenyl)ethan-1-one O-(2-chloro-6-((4,6-dimethoxypyrimidin-2-yl)thio)benzoyl)oxime, with a yield of 74.3%, and a melting point of 81° C.-86° C.

$^1$H NMR. (400 MHz, CDCl$_3$): δ 7.95 (d, J=7.1 Hz, 2H), 7.73-7.66 (m, 2H), 7.54 (dd, J=11.1, 4.0 Hz, 2H), 7.46 (t, J=7, 9 Hz, 1H), 5.80 (s, 1H), 3.80 (s, 6H), 2.30 (s, 3H).

$^{13}$C NMR (75 MHz, CDCl$_3$): δ 180.90, 169.02, 163.12, 162.86, 137.90, 136.18, 135.35, 131.75, 131.66 (d, J=13.0 Hz), 131.10 (d, J=32.47 Hz), 130.58, 130.44 (d, 1=2.4 Hz), 129.49, 129.19, 127.36 (q, J=3.7 Hz), 124.00 (q, J=3.9 Hz), 123.76 (q, J=27.1 Hz), 86.62, 54.08, 14.43.

Embodiment 11: Preparation of 4-trifluoromethyl acetophenone oxime 4-trifluoromethyl acetophenone (10.0 g, 53.1 mmol), hydroxylamine hydrochloride (5.5 g, 79.7 mmol), 80 mL of isopropanol, 20 mL of water and 10 mL of pyridine are added to a 250 mL reaction flask, and a reflux reaction is performed at 80° C. for 1 hour. After the reaction, the solvent is evaporated under decompression, washed with water, filtered with suction, and dried to obtain 10.3 g of white solid 4-trifluoromethyl acetophenone oxime, with a yield of 95.5%.

Embodiment 12: Preparation of (E)-1-(4-(trifluoromethyl)phenyl)ethan-1-one O-(2-chloro-6-((4,6-dimethoxypyrimidin-2-yl)thio)benzoyl)oxime (F)

2-chloro-6-((4,6-dimethoxypyrimidin-2-yl)thio)benzoic acid (10.0 g, 30.6 mmol), EDCI (7.0 g, 36.7 mmol), HOBt (0.21 g, 1.5 mmol), and 90 mL, of dichloromethane are added in a 250 mL reaction flask, then 4-trifluoromethyl acetophenone oxime (6.2 g, 30.6 mmol) in dichloromethane is added dropwise, and then reacted at 25° C. for 6 hours. After the reaction is completed, a suction filtration is performed first, and the filtrate is subjected to decompression distillation and recrystallization to obtain 12.1 g of white solid (E)-1-(4-(trifluoromethyl)phenyl)ethan-1-one-O-(2-chloro-6-((4,6-dimethoxypyrimidin-2-yl)thi o)benzoyl)oxime, with a yield of 77.3%, and a melting point of 86° C.-90° C.

$^1$H NMR (400 MHz, CDCl$_3$): δ 7.84 (d, J=8.2 Hz, 2H), 7.72-7.61 (m, 3H), 7.57-7.49 (m, 1H), 7.47 (d, J=7.9 Hz, 1H), 5.80 (s, 1H), 3.80 (s, 6H), 2.29 (s, 3H).

$^{13}$C NMR (75 MHz, CDCl$^3$): δ 180.89, 169.01, 163.19, 162.86, 137.89, 137.88, 136.20, 132.46 (t, J=32.47 Hz), 131.54 (d, J=9.8 Hz), 129.43, 129.15, 127.56, 125.53 (q, J=3.7 Hz), 125.45, 121.97, 86.62, 54.11, 14.46.

Embodiment 13: Preparation of 2-nitroacetophenone oxime 2-nitroacetophenone (10.0 g, 60.5 mmol), hydroxylamine hydrochloride (6.3 g, 90.8 mmol) and 80 mL of methanol are added to a 250 mL reaction flask, and then a 20% sodium hydroxide aqueous solution (18.2 g, 90.8 mmol) is added dropwise, and a reflux reaction is performed at 65° C. for 2 hours, After the reaction, the solvent is evaporated under decompression, washed with water, filtered with suction, and dried to obtain 10.1. g of white solid 2-nitroacetophenone oxime, with a yield of 92.7%, Embodiment 14: Preparation of (E)-1-(2-nitrophenyl)ethan-1-one O-(2-chloro-6-((4,6-dimethoxypyrimidin-2-yl)thio)benzoyl)oxime (G)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 2-nitroacetophenone oxime (5.5 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 11.8 g of white solid (E)-1-(2-nitrophenyl)ethan-1-one O-(2-chloro-6-((4,6-dimethoxypyrimidin-2-yl)thio)benzoyl)oxime, with a yield of 78.9%, and a melting point of 130° C.-134° C.
$^1$H NMR (400 MHz, CDCl$_3$): δ 8.15 (d, J=8.1 Hz, 1H), 7.68 (ddd, J=15.6, 7.8, 1.0 Hz, 2H), 7.60 (td, J=8.1, 1.4 Hz, 1H), 7.52 (m, 2H), 7.44 (t, J=7.9 Hz, 1H), 5.70 (s, 1H), 3.71 (s, 6H), 2.19 (s, 3H).
$^{13}$C NMR (75 MHz, CDCl$_3$): δ 170.90, 169.10, 165.15, 162.98, 147.00, 137.75, 136.19, 134.07, 131.70, 131.65, 130.86, 130.64, 130.63, 130.49, 129.54, 124.95, 86.57, 54.10, 18.17.

Embodiment 15: Preparation of 3-nitroacetophenone oxime 3-nitroacetophenone (10.0 g, 60.5 mmol), hydroxylamine hydrochloride (6.3 g, 90.8 mmol) and 80 mL of methanol are added to a 250 mL reaction flask, and then a 20% sodium acetate aqueous solution (37.2 g, 90.8 mmol) is added dropwise, and a reflux reaction is performed at 25° C. for 2 hours. After the reaction, the solvent is evaporated under decompression, washed with water, filtered with suction, and dried to obtain 10.4 of white solid 3-nitroacetophenone oxime, with a yield of 95.4%.

Embodiment 16: Preparation of (E)-1-(3-nitrophenyl)ethan-1-one O-(2-chloro-6-((4,6-dimethoxypyrimidin-2-yl)thio)benzoyl)oxime (H)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 3-nitroacetophenone oxime (5.5 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 11.4 g of white solid (E)-1-(3-nitrophenyl)ethan-1-one O-(2-chloro-6-((4,6-dimethoxypyrimidin-2-yl)thio)benzoyl)oxime, with a yield of 76.2%, and a melting point of 155° C.-159° C.
$^1$H NMR (400 MHz, CDCl$_3$): δ 8.50 (s, 1H), 8.28 (d, J=7.9 Hz, 1H), 8.13 (d, J=7.8 Hz, 1H), 7.67 (d, J=7.6 Hz, 1H), 7.62-7.51 (m, 2H), 7.46 (t, J=7.9 Hz, 1H), 5.68 (s, 1H), 3.69 (s, 6H), 2.32 (s, 3H).
$^{13}$C NMR (75 MHz, CDCl$_3$): δ 169.86, 167.92, 161.91, 161.00, 147.30, 136.66, 135.17, 131.91, 130.53, 129.68, 129.47, 128.71, 128.45, 124.33, 121.11, 85.58, 53.07, 13.34.

Embodiment 17: Preparation of 4-nitroacetophenone oxime 4-nitroacetophenone (10.0 g, 60.5 mmol), hydroxylamine hydrochloride (6.3 g, 90.8 mmol) and 80 mL of isopropanol are added to a 250 mL reaction flask, and then a 20% sodium carbonate aqueous solution (48.1 g, 90.8 mmol) is added dropwise, and reacted at 25° C. for 2 hours. After the reaction, the solvent is evaporated under decompression, washed with water, filtered with suction, and dried to obtain 10.2 g of white solid 4-nitroacetophenone oxime, with a yield of 93.6%.

Embodiment 18: Preparation of (E)-1-(4-nitrophenyl)ethan-1-one O-(2-chloro-6-((4,6-dimethoxypyrimidin-2-yl)thio)benzoyl)oxime (I)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 4-nitroacetophenone oxime (5.5 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 12.4 g of white solid (E)-1-(4-nitrophenyl)ethan-1-one O-(2-chloro-6-((4,6-dimethoxypyrimidin-2-yl)thio)benzoyl)oxime, with a yield of 82.9%, and a melting point of 153° C.-157° C.
$^1$H NMR (400 MHz, CDCl$_3$): δ 8.25 (d, J=8.9 Hz, 2H), 7.92 (d, J=8.9 Hz, 2H), 7.68 (dd, J=7.7, 1.0 Hz, 1H), 7.55 (dd, J=8.1, 0.9 Hz, 1H), 7.47 (t, J=7.9 Hz, 1H), 5.70 (s, 1H), 3.71 (s, 6H), 2.32 (s, 3H).
$^{13}$C NMR (75 MHz, CDCl$_3$): δ 170.90, 168.95, 162.94, 162.19, 149.09, 140.44, 137.65, 136.22, 131.57, 130.74, 130.52, 129.47, 128.20, 123.74, 86.62, 54.13, 14.49.

Embodiment 19: Preparation of 2-fluoroacetophenone oxime 2-fluoroacetophenone (10.0 g, 72.4 mmol), hydroxylamine hydrochloride (7.5 g, 108.6 mmol) and 80 mL of ethanol are added to a 250 mL reaction flask, and then a 20% sodium hydroxide aqueous solution (21.7 g, 108.6 mmol) is added dropwise, and reacted at 25° C. for 4 hours. After the reaction, the solvent is evaporated under decompression, washed with water, filtered with suction, and dried to obtain 10.5 g of white solid 2-fluoroacetophenone oxime, with a yield of 94.7%.

Embodiment 20: Preparation of (E)-1-(2-fluorophenyl)ethan-1-one O-(2-chloro-6-((4,6-dimethoxypyrimidin-2-yl)thio)benzoyl) oxime (J)

2-chloro-6-((4,6-dimethoxypyrimidin-2-yl)thio)benzoic acid (10.0 g, 30.6 mmol), DCC (7.6 g, 36.7 mmol), DMAP-1 (0.18 g, 1.5 mmol), and 90 mL of dichloromethane are added in a 250 mL reaction flask, then 2-fluoroacetophenone oxime (4.7 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 9.7 of white solid (E)-1-(2-fluorophenyl)ethan-1-one O-(2-chloro-6((4,6-dimethoxypyrimidin-2-yl)thio)benzoyl) oxime, with a yield of 68.6%, and a melting point of 87° C.-91° C.
$^1$H NMR (400 MHz, CDCl$_3$): δ 7.66 (d, J=7.7 Hz, 1H), 7.59 (s, 1H), 7.52 (d, J=7.4 Hz, 1H), 7.46-7.36 (m, 2H), 7.17-7.05 (m, 2H), 5.70 (s, 1H), 3.70 (s, 6H), 2.26 (d, J=2.8 Hz, 3H).

$^{13}$C NMR (75 MHz, CDCl$_3$): δ 170.89, 169.08, 163.21 (d, J=4.5 Hz), 162.47, 159.14, 137.92, 136.17, 132.14 (d, J=8.3 Hz), 131.59, 130.45 (d, J=3.0 Hz), 130.24 (d, J=2.3 Hz), 129.51, 124.34 (d, J=3.0 Hz), 123.30 (d, J=12.0 Hz), 116.36, 116.07, 86.62, 54.00, 16.98.

Embodiment 21: Preparation of 3-fluoroacetophenone oxime 3-fluoroacetophenone (10.0 g, 72.4 mmol), hydroxylamine hydrochloride (7.5 g, 108.6 mmol) and 80 mL of ethanol are added to a 250 mL reaction flask, and then a 20% sodium acetate aqueous solution (44.5 g, 108.6 mmol) is added dropwise, and reacted at 25° C. for 2 hours. After the reaction, the solvent is evaporated under decompression, washed with water, filtered with suction, and dried to obtain 10.1 g of white solid 3-fluoroacetophenone oxime, with a yield of 91.1%.

Embodiment Preparation of (E)-1-(3-fluorophenyl) ethan-1-one O-(2-chloro-6-((4,6-dimethoxypyrimidin-2-yl)thio)benzoyl) oxime (K)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 3-fluoroacetophenone oxime (4.7 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 11.6 g of white solid (E)-1-(3-fluorophenyl)ethan-1-one O-chloro-6((4,6-dimethoxypyrimidin-2-yl)thio)benzoyl) oxime, with a yield of 82.0%, and a melting point of 103° C.-107° C.

$^1$H NMR (400 MHz, CDCl$_3$): δ 7.67 (dd, J=7.7, 1.0 Hz, 1H), 7.52 (dd, J=8.1, 1.0 Hz, 1H), 7.49 (d, J=7.9 Hz, 1H), 7.44 (m, 2H), 7.35 (td, J=8.0, 5.9 Hz, 1H), 7.13 (td, J=8.3, 1.8 Hz, 1H), 5.69 (s, 1H), 3.70 (s, 6H), 2.25 (s, 3H).

$^{13}$C NMR (75 MHz, CDCl$_3$): δ 176.83, 173.41, 163.79 (d, J=77.3 Hz), 162.94 (d, J=3.0 Hz), 161.04, 137.99, 136.55 (d, J=7.5 Hz), 136.18, 131.51, 130.49 (d, J=7.5 Hz), 130.23, 130.12, 129.42, 122.90 (d, J=3.0 Hz), 117.75 (d, J=21.0 Hz), 114.13 (d, J=23.25 Hz), 86.59, 54.22, 14.29.

Embodiment 23: Preparation of 4-fluoroacetophenone oxime 4-fluoroacetophenone (10.0 g, 72.4 mmol), hydroxylamine hydrochloride (7.5 g, 108.6 mmol) and 80 mL of methanol are added to a 250 mL reaction flask, and then a 20% sodium acetate aqueous solution (44.5 g, 108.6 mmol) is added dropwise, and reacted at 25° C. for 2 hours. After the reaction, the solvent is evaporated under decompression, washed with water, filtered with suction, and dried to obtain 10.0 g of white solid 4-fluoroacetophenone oxime, with a yield of 90.2%.

Embodiment 24: Preparation of (E)-1-(4-fluorophenyl)ethan-1-one O-(2-chloro-6((4.6-dimethoxypyrimidin-2-yl)thio)benzoyl) oxime (L)

2-chloro-6-((4,6-dimethoxypyrimidin-2-yl)thio)benzoic acid (10.0 g, 30.6 mmol, DCC (7.6 g, 36.7 mmol), DMAP (0.18 g, 1.5 mmol), and 90 mL of dichloromethane are added in a 250 mL reaction flask, then 4-fluoroacetophenone oxime (4.7 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 11.6 g of white solid (E)-1-(4-fluorophenyl)ethan-1-one O-(2-chloro-6((4,6-dimethoxypyrimidin-2-yl)thio)benzoyl) oxime, with a yield of 82.3%, and a melting point of 102° C.-105° C.

$^1$H NMR (400 MHz, CDCl$_3$): δ 7.74 (dd, J=8.8, 5.3 Hz, 2H), 7.67 (dd, J=7.7, 0.9 Hz, 1H), 7.53 (dd, J=8.1, 0.9 Hz, 1H), 7.44 (t, J=7.9 Hz, 1H), 7.07 (t, J=8.7 Hz, 2H), 5.70 (s, 1H), 3.70 (s, 6H), 2.25 (s, 3H).

$^{13}$C NMR (75 MHz, CDCl$_3$): δ 170.88, 169.06, 166.02, 163.06, 163.0 (d, J=45.7 Hz), 138.05, 136.18, 131.51, 130.54, 130.47 (d, J=5.1 Hz), 129.41, 129.26 (d, J=8.6 Hz). 115.79, 115.50, 86.58, 54.08, 14.39.

Embodiment 25: Preparation of 2,4-dimethoxyacetophenone oxime 2,4-dimethoxyacetophenone (10.0 g, 55.5 mmol), hydroxylamine hydrochloride (5.8 g, 83.2 mmol) and 80 mL of methanol are added to a 250 mL reaction flask, and then a 20% sodium hydroxide aqueous solution (16.6 g, 83.2 mmol) is added dropwise, and reacted at 25° C. for 5 hours. After the reaction, the solvent is evaporated under decompression, washed with water, filtered with suction, and dried to obtain 10.2 g of white solid 2,4-dimethoxyacetophenone oxime, with a yield of 94.4%.

Embodiment 26: Preparation of (E)-1-(2,4-dimethoxyphenyl)ethan-1-one O-(2-chloro-6-((4,6-dimethoxypyrimidin-2-yl)thio)benzoyl)oxime (M)

2-chloro-6-((4,6-dimethoxypyrimidin-2-yl)thio)benzoic acid (10.0 g, 30.6 mmol), DCC (7.6 g, 36.7 mmol), DMAP (0.18 g, 1.5 mmol), and 90 mL of dichloromethane are added in a 250 mL reaction flask, then 2,4-dimethoxyacetophenone oxime (4.7 g, 30.6 mmol) in dichloromethane is added dropwise, and then reacted at 25° C. for 24 hours. After the reaction is completed, a suction filtration is performed first, and the filtrate is subjected to decompression distillation and recrystallization to obtain 12.2 g of white solid (E)-1-(2,4-dimethoxyphenyl)ethan-1-one O-(2-chloro-6-((4,6-dimethoxypyrimidin-2-yl)thio)benzoyl)oxime, with a yield of 79.3%, and a melting point of 125° C.-129° C.

$^1$H NMR (400 MHz, CDCl$_3$): δ 7.65 (d, J=7.7 Hz, 1H), 7.51 (d, J=8.0 Hz, 1H), 7.45-7.37 (m, 2H), 6.49-6.40 (m, 2H), 5.70 (s, 1H), 3.80 (d, J=9.4 Hz, 6H), 3.70 (s, 6H), 2.17 (s, 3H).

$^{13}$C NMR (75 MHz, CDCl$_3$): δ 170.85, 169.23, 166.28, 163.54, 162.63, 159.04, 138.39, 136.13, 131.52, 131.11, 130.36, 130.25, 129.39, 117.49, 104.37, 98.81, 86.53, 55.48, 55.44, 54.06, 17.42.

Embodiment 27: Herbicidal Activity Test

The pyrimidinylthio-benzoate compound of the present invention has good herbicidal activity and can be used as an effective active ingredient of herbicides to prepare various pesticide formulations, such as wettable powders, emulsions, water-dispersible granules, tablets, granules and the like.

The herbicidal activity of the herbicide prepared by the present invention is tested, and the results are as follows.

1. Test Reagent and Preparation 20 mg of the pyrimidinylthio-benzoate compound active pharmaceutical ingredients (APIs) is weighed with a 1/10, 000 analytical balance, dissolved with acetone (or DMF or DMSO), and diluted with a 0.1% Tween-80 aqueous solution to a concentration of 45 g a.i/hm$^2$.

2. Experimental Design

| Test item | Test target | | | | | | Processing capacity |
|---|---|---|---|---|---|---|---|
| Pot experiment | Echinochloa crusgalli | Eleusin eindica | Setaria viridis | Portulaca oleracea | Amaranthus retroflexus | Chenopodium album | 45 g a.i/hm$^2$ |

3. Test Method

The test soil is quantitatively filled to 4/5 of the pot, and subirrigation method is adopted at a bottom of the pot to moisten the soil. The test weed seeds are sown on the soil surface and cultivated in a greenhouse. When the gramineous weeds grow to 3-4 leaf stage and broadleaf weeds grow to 4-6 leaf stage, a stem and leaf spray method is used for treatment. On the 21$^{st}$ day after applying the herbicide, the above-ground part is taken to weigh the fresh weight, and the fresh weight inhibition rate is calculated according to the formula.

Fresh weight inhibition rate (%)=(control fresh weight−treated fresh weight)/control fresh weight×100%

Pyrithiobac-sodium is used as a positive control. The herbicidal activity of the target compound is screened. The dosage refers to the applied dosage of the pyrithiobac-sodium in the cotton field, i.e., 45 g a.i/hm$^2$, and the stem and leaf spray method is used for treatment. The results are shown in Table 1.

The pyrimidinylthio-benzoate compounds of the present invention are all novel and unreported compounds, and their inhibitory activity against weeds such as barnyard grass (*Echinochloa crusgalli*), goose grass (*Eleusine indica*), red-root amaranth (*Amaranthus retroflexus*), purslane (*Portulaca oleracea*), and lambsquarters (*Chenopodium album*) have been measured. Among them, the compounds containing the fluorine, the nitro group and the 2,4-dimethoxy group have better inhibitory activity on weeds, with inhibitory activities reaching more than 85%, or even 100% (except *Setaria viridis*), and higher than that of commercial herbicide pyrithiobac-sodium, showing excellent herbicidal efficacy.

4. Conclusion

In the present invention, pyrimidinylthio-benzoate compounds have been extensively studied, with the purpose of developing a compound with high efficiency, broad spectrum activity and safety. The results showed that the intro-

TABLE 1

Indoor herbicidal activity of the pyrimidinylthio-benzoate compound

| Compound | Inhibition rate (%) | | | | | |
|---|---|---|---|---|---|---|
| | Echinochloa crusgalli | Eleusine indica | Setaria viridis | Portulaca oleracea | Amaranthus retroflexus | Chenopodium album |
| A | 35.6 | 67.6 | 31.3 | 35.4 | 92.0 | 100 |
| B | 30.3 | 53.0 | 53.0 | 60.7 | 93.5 | 87.0 |
| C | 37.5 | 52.5 | 39.3 | 40.9 | 90.4 | 95.8 |
| D | 78.3 | 52.4 | 33.7 | 69.2 | 80.2 | 89.6 |
| E | 79.5 | 37.0 | 27.8 | 64.6 | 82.4 | 82.4 |
| F | 100 | 80.7 | 56.0 | 84.4 | 97.5 | 85.1 |
| G | 90.4 | 84.6 | 60.3 | 89.4 | 100 | 95.7 |
| H | 87.7 | 88.5 | 64.6 | 85.9 | 100 | 90.4 |
| I | 95.7 | 89.7 | 75.1 | 94.5 | 100 | 96.8 |
| J | 100 | 90.3 | 77.2 | 90.2 | 100 | 98.4 |
| K | 100 | 92.0 | 72.9 | 93.3 | 100 | 100 |
| L | 100 | 87.0 | 75.4 | 90.5 | 100 | 100 |
| M | 100 | 85.6 | 77.2 | 90.9 | 100 | 100 |
| Pyrithiobac-sodium | 60.6 | 44.7 | 65.4 | 96.8 | 95.2 | 93.9 |

As can be observed from the above Table 1, under 45 g a.i./hm$^2$, the pyrimidinylthio-benzoate compounds have a good inhibitory activity on weeds such as barnyard grass (*Echinochloa crusgalli*), goose grass (*Eleusine indica*), red-root amaranth (*Amaranthus retroflexus*), purslane (*Portulaca oleracea*), and lambsquarters (*Chenopodium album*), but not an obvious inhibitory effect on green bristlegrass (*Setaria viridis*). The inhibitory activity of the pyrimidinylthio-benzoate compounds on broadleaf weeds is generally better than that on gramineous weeds. The inhibitory rates of J, K, L and M on broadleaf weeds are higher than 90%, and are better than that of pyrithiobac-sodium.

duction of functional groups such as the fluorine, the nitro group, and the m-trifluoromethyl group all had better control effects on the tested weeds and could be used as candidate compounds for herbicides.

The foregoing descriptions are merely preferred embodiments of the present invention It should be noted that for those of ordinary skill in the art, several improvements and supplements can be made without departing from the present invention. These improvements and supplements shall fall within the protective scope of the present invention.

What is claimed is:

1. A pyrimidinylthio-benzoate compound with herbicidal activity, of formula (I):

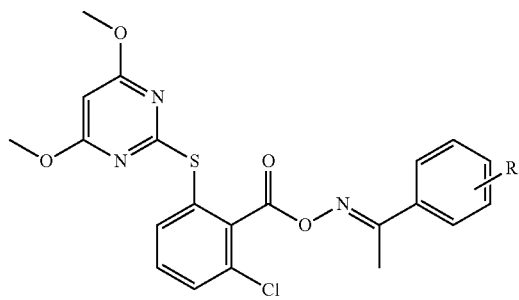

(I)

wherein R is one selected from the group consisting of an ortho-methyl group, a meta-methyl group, a para-methyl group, an ortho-trifluoromethyl group, a meta-trifluoromethyl group, a para-trifluoromethyl group, an ortho-nitro group, a meta-nitro group, a para-nitro group, an ortho-fluorine, a meta-fluorine, a para-fluorine and a 2,4-dimethoxy group;

and the pyrimidinylthio-benzoate compound has a chemical name and a chemical structural formula selected from the group consisting of:

A: (E)-1-(o-tolyl)ethan-1-one O-(2-chloro-6-((4,6-dimethoxypyrimidin-2-yl)thio)benzoyl) oxime

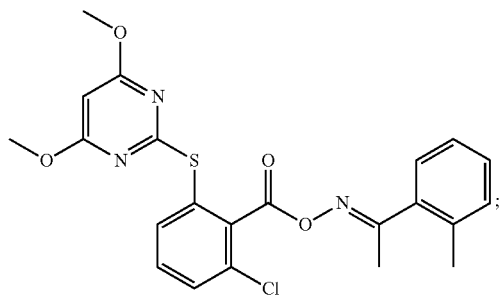

B: (E)-1-(m-tolyl)ethan-1-one O-(2-chloro-6-((4,6-dimethoxypyrimidin-2-yl)thio)benzoyl) oxime

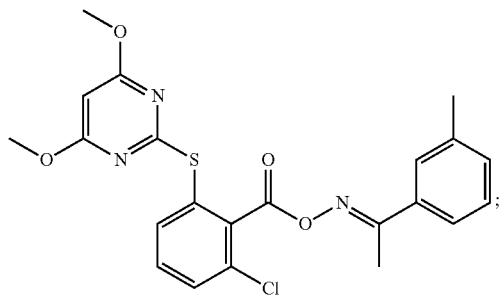 [SMILES: COc1cc(OC)nc(Sc2cccc(Cl)c2C(=O)O/N=C(\C)c2cccc(C)c2)n1]

C: (E)-1-(p-tolyl)ethan-1-one O-(2-chloro-6-((4,6-dimethoxypyrimidin-2-yl)thio)benzoyl) oxime

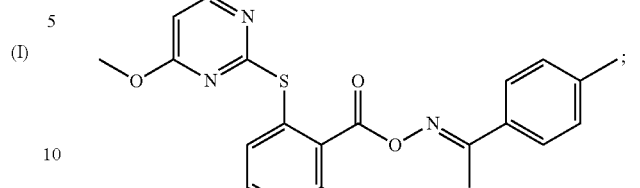

D: (E)-1-(2-(trifluoromethyl)phenyl)ethan-1-one O-(2-chloro-6-((4,6-dimethoxypyrimidin-2-yl)thio)benzoyl) oxime

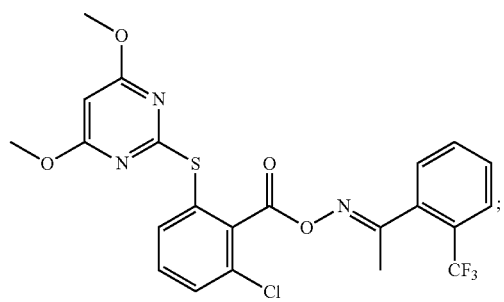

E: (E)-1-(3-(trifluoromethyl)phenyl)ethan-1-one O-(2-chloro-6-((4,6-dimethoxypyrimidin-2-yl)thio)benzoyl) oxime

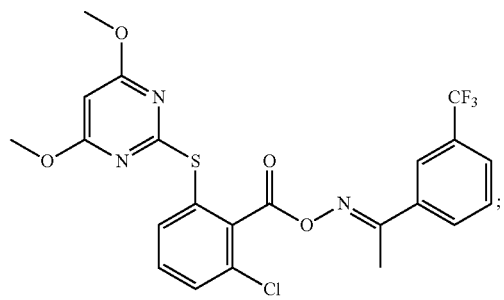 [SMILES: COc1cc(OC)nc(Sc2cccc(Cl)c2C(=O)O/N=C(\C)c2cccc(C(F)(F)F)c2)n1]

F: (E)-1-(4-(trifluoromethyl)phenyl)ethan-1-one O-(2-chloro-6-((4,6-dimethoxypyrimidin-2-yl)thio)benzoyl) oxime

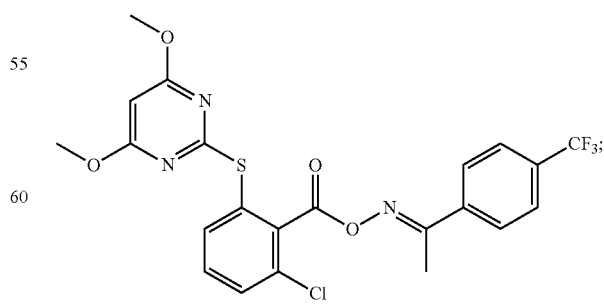

G: (E)-1-(2-nitrophenyl)ethan-1-one O-(2-chloro-6-((4,6-dimethoxypyrimidin-2-yl)thio)benzoyl)oxime

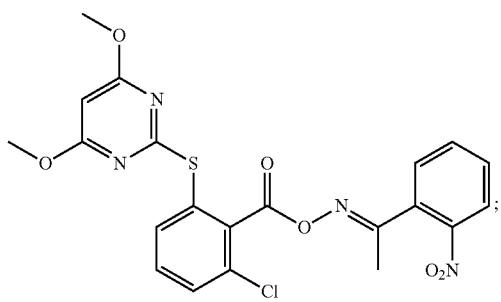 [SMILES: COc1cc(OC)nc(Sc2cccc(Cl)c2C(=O)O/N=C(\C)c2ccccc2[N+](=O)[O-])n1]

H: (E)-1-(3-nitrophenyl)ethan-1-one O-(2-chloro-6-((4,6-dimethoxypyrimidin-2-yl)thio)benzoyl)oxime

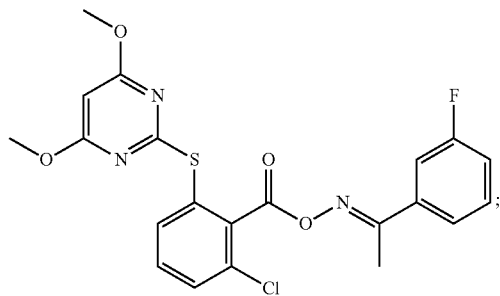

L: (E)-1-(4-fluorophenyl)ethan-1-one O-(2-chloro-6-((4,6-dimethoxypyrimidin-2-yl)thio)benzoyl) oxime

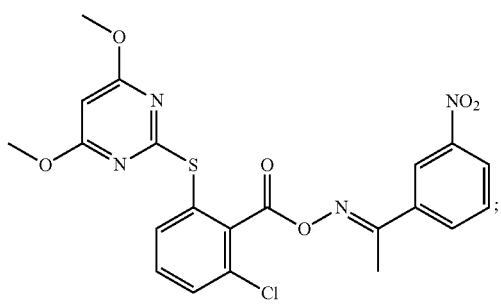 [SMILES: COc1cc(OC)nc(Sc2cccc(Cl)c2C(=O)O/N=C(\C)c2cccc([N+](=O)[O-])c2)n1]

I: (E)-1-(4-nitrophenyl)ethan-1-one O-(2-chloro-6-((4,6-dimethoxypyrimidin-2-yl)thio)benzoyl)oxime

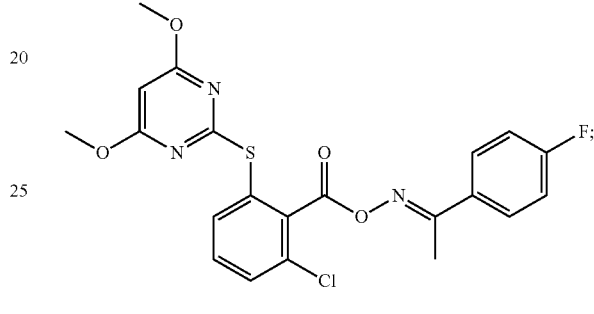

and
M: (E)-1-(2,4-dimethoxyphenyl)ethan-1-one O-(2-chloro-6-((4,6-dimethoxypyrimidin-2-yl)thio)benzoyl) oxime

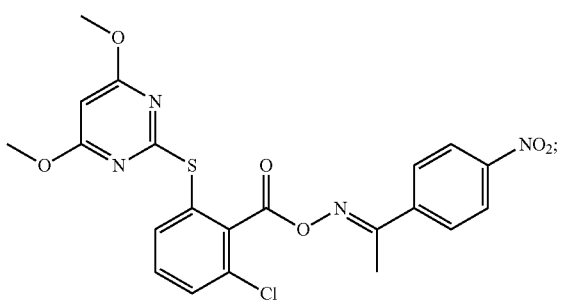 [SMILES: COc1cc(OC)nc(Sc2cccc(Cl)c2C(=O)O/N=C(\C)c2ccc([N+](=O)[O-])cc2)n1]

J: (E)-1-(2-fluorophenyl)ethan-1-one O-(2-chloro-6-((4,6-dimethoxypyrimidin-2-yl)thio)benzoyl) oxime

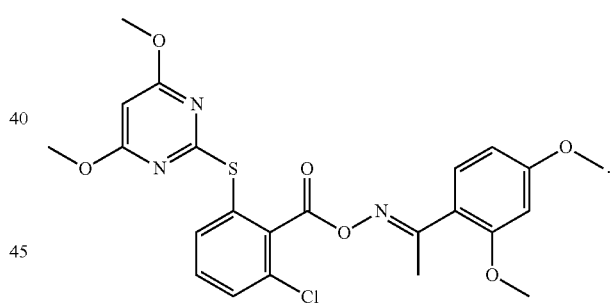

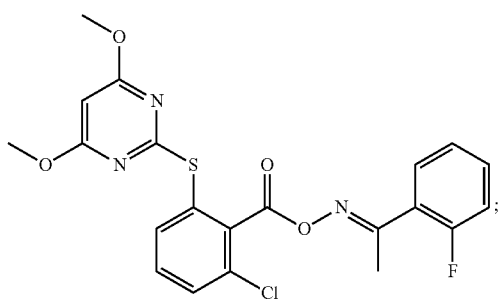

K: (E)-1-(3-fluorophenyl)ethan-1-one O-(2-chloro-6-((4,6-dimethoxypyrimidin-2-yl)thio)benzoyl) oxime 2. A method of preparing the pyrimidinylthio-benzoate compound according to claim 1, comprising the following steps:
   step A: preparing a substituted acetophenone oxime: adding an alcohol as an alcohol solvent to hydroxylamine hydrochloride and a substituted acetophenone to obtain a first mixture, and reacting the first mixture at 0° C.-80° C. for 1-5 hours under an alkaline condition to obtain the substituted acetophenone oxime; and
   step B: preparing the pyrimidinylthio-benzoate compound of formula (I): reacting 2-chloro-6-((4,6-dimethoxypyrimidin-2-yl)thio)benzoic acid and the substituted acetophenone oxime from step A in an organic solvent, in the presence of a dehydrating agent and a catalyst at 25° C. for 6-24 hours to obtain a second mixture; performing a suction filtration on the second mixture to obtain a filtrate, and subjecting the filtrate to a decompression distillation and a recrystallization to obtain the pyrimidinylthio-benzoate compound of formula (I).

3. The method according to claim 2, wherein the alcohol solvent in step A is one selected from the group consisting of methanol, ethanol and isopropanol; and
- a base for the alkaline condition in step A is one selected from the group consisting of sodium hydroxide, sodium carbonate, sodium acetate, triethylamine and pyridine; and
- a molar ratio of the substituted acetophenone, the hydroxylamine hydrochloride, the base, and the alcohol in step A is 1:1.5:1.5:8.

4. The method according to claim 2, wherein the organic solvent in step B is dichloromethane;
- the dehydrating agent in step B is one selected from the group consisting of N,N'-dicyclohexylcarbodiimide (DCC), 1-(3-dimethylaminopropyl)-3-ethylcarbodiimide hydrochloride (EDCI) and N,N'-diisoproplylcarbodiimide (DIC);
- the catalyst in step B is one selected from the group consisting of 4-dimethylaminopyridine (DMAP), 4-(1'-tetrahydro pyrrole)pyridine (4-PPY) and 1-hydroxybenzotriazole (HOBt); and
- a molar ratio of the 2-chloro-6-((4,6-dimethoxypyrimidin-2-yl)thio)benzoic acid, the substituted acetophenone oxime, the dehydrating agent, the catalyst, and the organic solvent in step B is 1:1:1.2:0.06:9.

5. A method of controlling weeds selected from the group consisting of: barnyard grass (*Echinochloa crusgalli*), goose grass (*Eleusine indica*), green bristlegrass (*Setaria viridis*), redroot amaranth (*Amaranthus retroflexus*), purslane (*Portulaca oleracea*), and lambsquarters (*Chenopodium album*) comprising applying to the weeds the pyrimidinylthio-benzoate compound according to claim 1.

* * * * *